United States Patent [19]

Knowles et al.

[11] Patent Number: 4,894,338
[45] Date of Patent: Jan. 16, 1990

[54] YEAST STRAINS PRODUCING CELLULOLYTIC ENZYMES AND METHODS AND MEANS FOR CONSTRUCTING THEM

[75] Inventors: Jonathan Knowles; Merja Penttilä; Tuula Teeri, all of Helsinki; Helena Nevalainen, Vaajakoski; Irma Salovuori, Järvenpää; Päivi Lehtovaara-Helenius, Helsinki, all of Finland

[73] Assignee: Oy Alko AB, Helsinki, Finland

[21] Appl. No.: 817,942

[22] PCT Filed: Apr. 12, 1985

[86] PCT No.: PCT/FI85/00039
§ 371 Date: Jan. 30, 1986
§ 102(e) Date: Jan. 30, 1986

[87] PCT Pub. No.: WO85/04672
PCT Pub. Date: Oct. 24, 1985

[30] Foreign Application Priority Data

Apr. 13, 1984 [FI] Finland .................................. 841500

[51] Int. Cl.[4] ....................... C12N 15/00; C12N 9/42; C12N 1/16; C07H 21/00
[52] U.S. Cl. ................................. 435/172.3; 435/209; 435/255; 435/320; 935/14; 935/28; 935/69; 935/48; 536/27
[58] Field of Search ...................... 435/172.3, 209, 255, 435/320; 935/14, 28, 48, 69; 536/27

[56] References Cited

U.S. PATENT DOCUMENTS 4,394,443  7/1983  Weissman et al. .................... 435/6 X
4,615,974  10/1986  Kingsman et al. ....................... 435/68

FOREIGN PATENT DOCUMENTS 0137280  4/1985  European Pat. Off. ............. 435/209

OTHER PUBLICATIONS

Fagerstam et al., *Febs Letters*, vol. 119, pp. 97–100, 1980.
Pettersson et al, Ekman-Days, Int. Symp. Wood Pulping Chemistry, vol. 3, pp. 39–42, 1981.
Teeri, T. et al, *Gene*, vol. 51, pp. 45–52, 1987.
Henrissat et al, *Bio/Technology*, vol. 3, pp. 722–726, Aug. 1985.
Chen, C. et al, Bio/Technology, vol. 5, pp. 274–278, Mar. 1987.
van Tilbeurgh et al., *Fed. Eur. Biochem. Societies* 169(2): 215–218 (1984).
Gong et al., *Adv. Chem. Ser.* 181:261–287 (1979).
Teeri et al., *Bio/Technology*, pp. 696–699, (Oct. 1983).
Shoemaker, Schwieckart et al., *Bio/Technology*, pp. 691–695 (Oct. 1983).
Shoemaker, Watt et al., *Bio/Technology*, pp. 687–690, (Oct. 1983).
Mellor et al., *Gene* 24:1–14 (1983).
James et al., *Proc. Bioenergy R & D Semin.* 3d: 135–139 (1981).
Seligy, V. et al, *Gene Expression in Yeast. Proceedings of the Alko Yeast Symposium*, Helsinki, 1983, (ed. by M. Korholac E. Vaisanen), pp. 167–185.

Primary Examiner—Jayme A. Huleatt
Attorney, Agent, or Firm—Saidman, Sterne, Kessler & Goldstein

[57] ABSTRACT

The full length DNA sequence encoding the mature cellobiohydrolase II(CHBII), as well as the DNA sequence encoding the CBHII signal sequence, have been isolated and cloned from the fungus *Trichoderma reesei*. Recombinant vectors comprising these sequences, and yeast hosts transformed with such vectors are disclosed. Also disclosed are methods for constructing the vectors and hosts according to the invention, as well as methods for expressing the disclosed sequences. CBHII is involved in hydrolysis of cellulose.

13 Claims, 10 Drawing Sheets

```
                                                EcoRI    CBH II CDNA
                                      ACCATGATTACGAATTCCCCTTGTAAGATCACCCTCTGTGTATTGCACC
                                                    pUC8
─CBH II signal sequence──────────────────────────────────────┐Hind III
ATGATTGTCGGCATTCTCACCACGCTGGCTACGCTGGCCACACTCGCAGCTAGTGTGCCTCTAGAGGAGCGGCAAGCTTGCTCAAGCGTC
MetIleValGlyIleLeuThrThrLeuAlaThrLeuAlaAlaSerValProLeuGluGluArgGlnAlaCysSerSerVal              30
                                                                     CBHII mature protein
                                                         Acc I
TGGGGCCAATGTGGTGGCCAGAATTGGTCGGGTCCGACTTGCTGTGCTTCCGGAAGCACATGCGTCTACTCCAACGACTATTACTCCCAG
TrpGlyGlnCysGlyGlyGlnAsnTrpSerGlyProThrCysCysAlaSerGlySerThrCysValTyrSerAsnAspTyrTyrSerGln   60

Acc I                                              Sac I
TGTCTTCCCGGCGCTGCAAGCTCAAGCTCGTCCACGCGCGCCGCGTCGACGACTTCTCGAGTATCCCCCACAACATCCCGGTCGAGCTCC
CysLeuProGlyAlaAlaSerSerSerSerSerThrArgAlaAlaSerThrThrSerArgValSerProThrThrSerArgSerSerSer   90

GCGACGCCTCCACCTGGTTCTACTACTACCAGAGTACCTCCAGTCGGATCGGGAACCGCTACGTATTCAGGCAACCCTTTTGTTGGGGTC
AlaThrProProProGlySerThrThrThrArgValProProValGlySerGlyThrAlaThrTyrSerGlyAsnProPheValGlyVal  120

Pst I Pvu II
ACTCCTTGGGCCAATGCATATTACGCCTCTGAAGTTAGCAGCCTCGCTATTCCTAGCTTGACTGGAGCCATGGCCACTGCTGCAGCAGCT
ThrProTrpAlaAsnAlaTyrTyrAlaSerGluValSerSerLeuAlaIleProSerLeuThrGlyAlaMetAlaThrAlaAlaAlaAla  150

GTCGCAAAGGTTCCCTCTTTTATGTGGCTAGATACTCTTGACAAGACCCCTCTCATGGAGCAAACCTTGGCCGACATCCGCACCGCCAAC
ValAlaLysValProSerPheMetTrpLeuAspThrLeuAspLysThrProLeuMetGluGlnThrLeuAlaAspIleArgThrAlaAsn  180

AAGAATGGCGGTAACTATGCCGGACAGTTTGTGGTGTATGACTTGCCGGATCGCGATTGCGCTGCCCTTGCCTCGAATGGCGAATACTCT
LysAsnGlyGlyAsnTyrAlaGlyGlnPheValValTyrAspLeuProAspArgAspCysAlaAlaLeuAlaSerAsnGlyGluTyrSer  210

ATTGCCGATGGTGGCGTCGCCAAATATAAGAACTATATCGACACCATTCGTCAAATTGTCGTGGAATATTCCGATATCCGGACCCTCCTG
IleAlaAspGlyGlyValAlaLysTyrLysAsnTyrIleAspThrIleArgGlnIleValValGluTyrSerAspIleArgThrLeuLeu  240

GTTATTGAGCCTGACTCTCTTGCCAACCTGGTGACCAACCTCGGTACTCCAAAGTGTGCCAATGCTCAGTCAGCCTACCTTGAGTGCATC
ValIleGluProAspSerLeuAlaAsnLeuValThrAsnLeuGlyThrProLysCysAlaAsnAlaGlnSerAlaTyrLeuGluCysIle  270

Pvu II
AACTACGCCGTCACACAGCTGAACCTTCCAAATGTTGCGATGTATTTGGACGCTGGCCATGCAGGATGGCTTGGCTGGCCGGCAAACCAA
AsnTyrAlaValThrGlnLeuAsnLeuProAsnValAlaMetTyrLeuAspAlaGlyHisAlaGlyTrpLeuGlyTrpProAlaAsnGln  300

Sac I
GACCCGGCCGCTCAGCTATTTGCAAATGTTTACAAGAATGCATCGTCTCCGAGAGCTCTTCGCGGATTGGCAACCAATGTCGCCAACTAC
AspProAlaAlaGlnLeuPheAlaAsnValTyrLysAsnAlaSerSerProArgAlaLeuArgGlyLeuAlaThrAsnValAlaAsnTyr  330

Acc I
AACGGGTGGAACATTACCAGCCCCCCATCGTACACGCAAGGCAACGCTGTCTACAACGAGAAGCTGTACATCCACGCTATTGGACCTCTT
AsnGlyTrpAsnIleThrSerProProSerTyrThrGlnGlyAsnAlaValTyrAsnGluLysLeuTyrIleHisAlaIleGlyProLeu  360

Pvu I
CTTGCCAATCACGGCTGGTCCAACGCCTTCTTCATCACTGATCAAGGTCGATCGGGAAAGCAGCCTACCGGACAGCAACAGTGGGGAGAC
LeuAlaAsnHisGlyTrpSerAsnAlaPhePheIleThrAspGlnGlyArgSerGlyLysGlnProThrGlyGlnGlnTrpGlyAsp    390

TGGTGCAATGTGATCGGCACCGGATTTGGTATTCGCCCATCCGCAAACACTGGGGACTCGTTGCTGGATTCGTTTGTCTGGGTCAAGCCA
TrpCysAsnValIleGlyThrGlyPheGlyIleArgProSerAlaAsnThrGlyAspSerLeuLeuAspSerPheValTrpValLysPro  420

GGCGGCGAGTGTGACGGCACCAGCGACAGCAGTGCGCCACGATTTGACTCCCACTGTGCGCTCCCAGATGCCTTGCAACCGGCGCCTCAA
GlyGlyGluCysAspGlyThrSerAspSerSerAlaProArgPheAspSerHisCysAlaLeuProAspAlaLeuGlnProAlaProGln  450
                                                                         STOP
GCTGGTGCTTGGTTCCAAGCCTACTTTGTGCAGCTTCTCACAAACGCAAACCCATCGTTCCTGTAAGGCTTTCGTGACCGGGCTTCAAAC
AlaGlyAlaTrpPheGlnAlaTyrPheValGlnLeuLeuThrAsnAlaAsnProSerPheLeu                             471
                Acc I
AATGATGTGCGATGGTGTGGTTCCCGGTTCGCGGAGTCTTTGTCTACTTTGGTTGTCTGTCGCAGGTCGGTAGACCGCAAATGAGCAACT

GATGGATTGTTGCCAGCGATACTATAATTCACATGGATGGTCTTTGTCGATCAGTAGGCTAGAGAGAGAGAGAGAACATCTATCCACAAT polyA   Bam HI
GTCGAGTGTCTATT(A)₁₃GGGGATCC
              pUC8
```

Fig. 5

```
                                                       pUC8
                                                    ←―――――――― CCCCCCTATCTTAGTCCTTCTTGTTGTCCCAAA
   ―――――――――ENDO II signal sequence―――――――――――――――――――――              Kpn I
ATGGCGCCCTCAGTTACACTGCCGTTGACCACGGCCATCCTGGCNATTGCCCGGCTCGTCGCCGCCCAGCAACCGGGTACCAGCACCCCC
MetAlaProSerValThrLeuProLeuThrThrAlaIleLeuAlaIleAlaArgLeuValAlaAlaGlnGlnProGlyThrSerThrPro      30

GAGGTCCATCCCAAGTTGACAACCTACAAGTGTACAAAGTCCGGGGGGTGCGTGGCCCAGGACACCTCGGTGGTCCTTGACTGGAACTAC
GluValHisProLysLeuThrThrTyrLysCysThrLysSerGlyGlyCysValAlaGlnAspThrSerValValLeuAspTrpAsnTyr      60

CGCTGGATGCACGACGCAAACTACAACTCGTGCACCGTCACCGGCGGCGTCAACACCACGCTCTGCCCTGACGAGGCGACCTGTGGCAAG
ArgTrpMetHisAspAlaAsnTyrAsnSerCysThrValAsnGlyGlyValAsnThrThrLeuCysProAspGluAlaThrCysGlyLys     90
           Sal I
AACTGCTTCATCCAGGGCGTCGACTACGCCGCCTCGGGCGTCACGACCTCGGGCAGCAGCCTCACCATGAACCAGTACATGCCCAGCAGC
AsnCysPheIleGlnGlyValAspTyrAlaAlaSerGlyValThrThrSerGlySerSerLeuThrMetAsnGlnTyrMetProSerSer    120

TCTGGCGGCTACAGCAGCGTCTCTCCTCGGCTGTATCTCCTGGACTCTGACGGTGAGTACGTGATGCTGAAGCTCAACGGCCAGGAGCTG
SerGlyGlyTyrSerSerValSerProArgLeuTyrLeuLeuAspSerAspGlyGluTyrValMetLeuLysLeuAsnGlyGlnGluLeu    150
       Sal I
AGCTTCGACGTCGACCTCTCTGCTCTGCCGTGTGGAGAGAACGGCTCGCTCTACCTGTCTCAGATGGACGAGAACGGGGGCGCCAACCAG
SerPheAspValAspLeuSerAlaLeuProCysGlyGluAsnGlySerLeuTyrLeuSerGlnMetAspGluAsnGlyGlyAlaAsnGln    180

TATAACACGGCCGGTGCCAACTACGGGAGCGGCTACTGCGATGCTCAGTGCCCCGTCCAGACATGGAGGAACGGCACCCTCAACACTAGC
TyrAsnThrAlaGlyAlaAsnTyrGlySerGlyTyrCysAspAlaGlnCysProValGlnThrTrpArgAsnGlyThrLeuAsnThrSer   210
                                            Xho I
CACCAGGGCCAGGGCTTCTGCTGCAACGAGATGGATATCCTGGAGGGCAACTCGAGGGCGAATGCCTTGACCCCTCACTCTTGCACGGCC
HisGlnGlyGlnGlyPheCysCysAsnGluMetAspIleLeuGluGlyAsnSerArgAlaAsnAlaLeuThrProHisSerCysThrAla    240

ACGGCCTGCGACTCTGCCGGTTGCGGCTTCAACCCCTATGGCAGCGGCTACAAAAGCTACTACGGCCCCGGAGATACCGTTGACACCTCC
ThrAlaCysAspSerAlaGlyCysGlyPheAsnProTyrGlySerGlyTyrLysSerTyrTyrGlyProGlyAspThrValAspThrSer    270

AACACCTTCACCATCATCACCCAGTTCAACACGGACAACGGCTCGCCCTCGGGCAACCTTGTGAGCATCACCCGCAAGTACCAGXXXXXX
LysThrPheThrIleIleThrGlnPheAsnThrAspAsnGlySerProSerGlyAsnLeuValSerIleThrArgLysTyrGln......    300
Sal I
GTCGACATCCCCAGCGCCCAGCCCGGCGGCGACACCATCTCGTCCTGCCCGTCCGCCTCAGCCTACGGCGGCCTCGCCACCATGGGCAAG
ValAspIleProSerAlaGlnProGlyGlyAspThrIleSerSerCysProSerAlaSerAlaTyrGlyGlyLeuAlaThrMetGlyLys    330

GCCCTGAGCAGCGGCATGGTGCTCGTGTTCAGCATTTGGAACGACAACAGCCAGTACATGAACTGGCTCGACAGCGGCAACGCCGGCCCC
AlaLeuSerSerGlyMetValLeuValPheSerIleTrpAsnAspAsnSerGlnTyrMetAsnTrhLeuAspSerGlyAsnAlaGlyPro    360
Pst I
TGCAGCAGCACCGAGGGCAACCCATCCAACATCCTGGCCAACAACCCCAACACGCACGTCGTCTTCTCCAACATCCGCTGGGGAGACATT
CysSerSerThrGluGlyAsnProSerAsnIleLeuAlaAsnAsnProAsnThrHisValValPheSerAsnIleArgTrpGlyAspIle    390
                          Sac I
GGGTCTACTACGAACTCGACT....x......x..GAGCTCGACGACTTCGAGCAGCCCGAGCTGCACGCAGACTCACTGGGGGCAGTGC
GlySerThrThrAsnSerThr.............SerSerThrThrSerSerSerProSerCysThrGlnThrHisTrpGlyGlnCys     420
                                                           ↓                    STOP
GGTGGCATTGGGTACAGCGGGTGCAAGACGTGCACGTCGGGCACTACGTGCCAGTATAGCAACGACTACTACTCGCAATGCCTTTAGAGC
GlyGlyIleGlyTyrSerGlyCysLysThrCysThrSerGlyThrThrCysGlnTyrSerAsnAspTyrTyrSerGlnCysLeuxxx      450
                    Sac I
GTTGACTTGCCTCTGGTCTGTCCAGACGGGGGCACGATAGAATGCGGGCACGCAGGGAGCTCGTAGACATTGGGCTTAATATATAAGACA POLY A   pUC 8
TGCTATGTTGTATCTACATTAGCAAATGACAAACAAATGAAAAAGAACTTATCAAGC(A)₂₅  ――――――→
```

Fig. 6

YEAST STRAINS PRODUCING CELLULOLYTIC ENZYMES AND METHODS AND MEANS FOR CONSTRUCTING THEM

BACKGROUND OF THE INVENTION

Three different classes of enzymatic activity have been shown to be required for the complete hydrolysis of cellulose to glucose. The two major activities involved in cellulose solubilization are endoglucanase (EC 3.2.1.4) and cellobiohydrolase (EC 3.2.1.91) (1, 2). For the production of glucose a third type of activity, cellobiase or β-glucosidase (EC 3.2.1.21) is also required. The precise manner in which these three different classes of enzyme interact to bring about the complete hydrolysis of cellulose is not yet clear.

Same filamentous fungi produce a number of different isoenzymes of each class of cellulolytic enzyme which apparently interact synergistically in hydrolysis (3, 4, 5, 6).

Trichoderma has been shown to produce at least two immunologically distinct cellobiohydrolases CBH I and CBH II, at least 2 endoglucanases, ENDO II and ENDO III, and a β-glucosidase. While enzymatic hydrolysis of cellulose proceeds most rapidly in the presence of all these enzymes, CBH I alone is able to degrade crystalline cellulose to glucose and cellobiose (7, 8, 9).

Two groups have reported the molecular cloning of the *T. reesei* gene for CBH I and the complete sequence of this gene is known (10, 11).

Yeast is an important industrial organism and is used for brewing, wine making, baking, ethanol production, single cell protein production and more recently for the production of pharmaceuticals such as interferon, growth hormone and Hepatitis B virus antigen. Yeast do not produce enzymes that degrade cellulose. The development of yeast strains able to hydrolyse cellulose would make possible improvements in existing processes where cellulose or glucans are present in the raw material used. As important would be the possibility of developing new processes not currently possible.

In filtration and clarification of beer high molecular weight β-glucans originating from barley grain cause problems. In the brewing industry microbial β-glucanases are used to remove these β-glucans. If the yeast used in the production of beer were able to produce endoglucanases, the filterability of beer would significantly be improved and the cost of filtering would decrease. By transferring individual fungal cellulase genes to yeast it is possible to produce yeast strains that produce only one cellulase enzyme. Such yeast strains would produce enzymes for use in, for example the pulp and paper industry. Cellulose used in paper making could be swelled by pretreating with one cellulase enzyme, which would bring about swelling without excessive hydrolysis of cellulose.

There are two ways in which a foreign gene can be expressed in yeast. The simplest is to join the whole gene from the chromosome of the donor organism to a yeast vector and transform a yeast cell. If the yeast genetic system recognizes the appropriate sequences in the transferred gene the gene will be expressed. However, in practice this is rare and depends at least in part on the genetic distance between the donor organism and the yeast.

For example, of the five genes from *Aspergillus niger* tested in *Saccharomyces cerevisiae*, only one of these was found to express (12). Therefore it cannot be assumed that heterologous genes will automatically be expressed in yeast.

The second method of obtaining expression of genes in yeast is by connecting either the chromosomal gene or a cDNA copy of the messenger RNA coding for the desired gene to a yeast promotor sequence. In this way, human eukaryote interferon (13), hepatitis B virus surface antigen (14), bovine rennin (15), and mouse α-amylase (16) have all been expressed in yeast.

These and other studies show that while expression of the cDNA or gene is always obtained, the amount and cellular location of the product is very difficult to predict in the absence of experimentation. Montenecourt (1) outlined a number of possible cloning strategies for cloning cellulase genes from *T. reesei* but did not describe the methods to be used to achieve the goal.

SUMMARY OF THE INVENTION

In accordance with this invention described are yeast strains capable of producing cellulolytic enzymes, methods for construction of these strains, recombinant DNA vectors needed in the construction of these strains, methods used in the construction of these vectors, and cDNA copies of cellulolytic enzymes coding genes.

Chromosomal genes coding for three different cellulases, CBH I, CBH II and ENDO II were isolated from a λ phage gene library of *T. reesei* by differential hybridisation. Fragments of these genes were used to isolate full length cDNAs from a *T. reesei* cDNA library.

cDNAs for the three cellulases CBH I, CBH II and ENDO II and the CBH I gene were transferred to suitable 2 μyeast plasmids. When used to transform suitable yeast strains, they directed the expression and secretion of the respective cellulase enzyme. The cellulases produced by the yeast were shown to have similar activities to the native fungal enzyme.

A cellulolytic yeast strain *Saccharomyces cerevisiae* VTT-RC-84001 produced in accordance with the present invention has been deposited in the National Collection of Yeast Cultures, Norwich, United Kingdom, under the deposit number NCYC No. R 128 since Apr. 6, 1984.

BRIEF DESCRIPTION OF THE DRAWINGS

The present invention is described below in greater detail with reference to the accompanying drawings.

FIG. 5 shows the cDNA sequence of the CBH II gene of *T. reesei* from plasmid pTTO9.

FIG. 6 shows the cDNA sequence of the ENDO II gene of *T. reesei* from plasmid pTT11. The positions of introns found in chromosomal copy of rhe gene are marked with arrow (↓).

DETAILED DESCRIPTION

Figure 1:
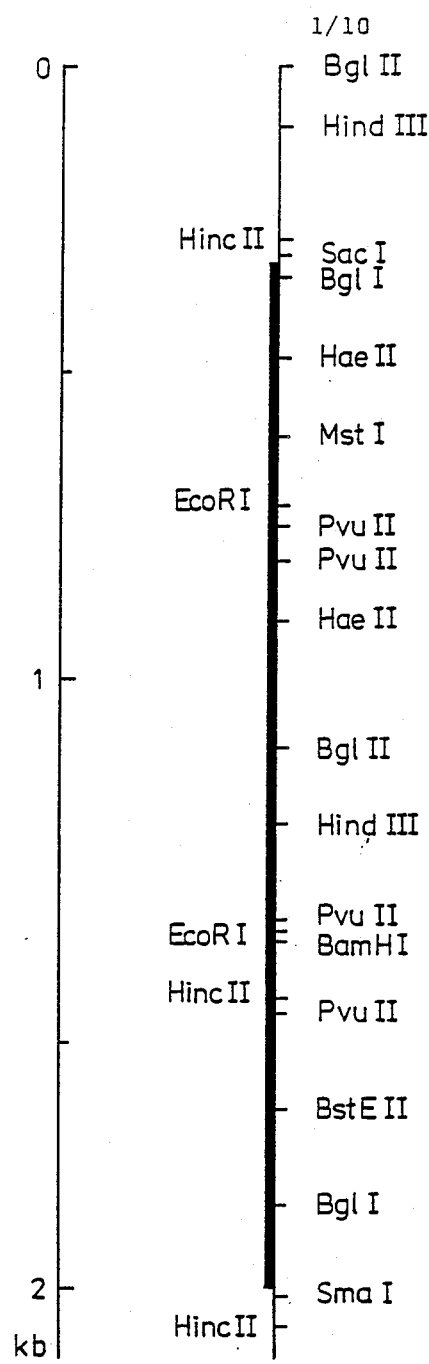
FIG. 1 shows the restriction map of *T. reesei* cellobiohydrolase I (CBH I) chromosomal gene. The coding region is marked with thickened line.

The definitions used in this detailed description are as defined in the Gilbert and Talmadge U.S. Pat. No. 4,338,397.

Materials

*Bacterial and fungal strains, plasmids, and phage.* T. reesei strain VTT-D-80133, a mutant strain with improved production of cellulolytic enzymes derived from QM 9414 (17) after several successive mutation steps (18), was used for isolation of the genes from cellobiohydrolase I (CBH I), cellobiohydrolase II (CBH II) and endoglucanase II (ENDO II).

*Escherichia coli* strains Q358 and Q359 and the phage λ 1059, used in the construction of the *T. reesei* gene bank were provided by Dr. J. Karn (19). E. coli HB 101 was used as a host in 5 transformation with the plasmid pBR 322. *E. coli* JM 101 and the phage M 13 mp 7 (20) and the plasmids pUC 8 and pUC 9 (21), used in the dideoxy sequencing, were from the laboratory of F. Sanger. Yeast strains used were *Saccharomyces cerevisiae* OL1 (Mata leu 2-3 leu 2-112 his 3-11 his 3-15 ura 3-251 ura 3-373) (22) and *S. cerevisiae* MT302-lc (Mata arg 5-6 leu 2-3 leu 2-112 his 3-11 his 3-15 pep 4-3 ade 1) (23).

A 12 kb cosmid p3030 obtained from Barbara Hohn, which replicates both in *E. coli* and in yeast was used as vector for transferring the chromosomal copy of CBH I to yeast. Cosmid p3030 contains genes for ampicillin and tetracycline resistance in *E. coli* and the his3 gene for selection in yeast. The vector contains a cos site which enables it to be packaged into infective λ phage particles in vitro and the yeast 2 μ EcoD fragment. Yeast expression vector containing the phosphoglycerokinase (PGK) gene promoter was used for expression of the cDNA copies of cellulase genes in yeast (23).

Enzymes. Restriction enzymes were purchased from Amershain (UK), Boehringer Mannheim (FDR) and Bethesda Research Laboratories (Gaithersburg, Md.) and used according to the manufacturers. instructions. T4 ligase and the DNA polymerase I large subunit were from Biolabs and the calf intestine phosphatase from Boehringer Mannheim. Reverse transcriptase was from Dr. J. W. Beard (Life Sciences Inc., St. Petersburg, Fla.). Protoplasting enzyme, Zymolyase 60000 was obtained from Kirin Brewery Co., Japan. Klenow fragment of *E. coli* polymerase I was from Boehringer Mannheim.

General growth media. *E. coli* HB1O1 was grown in L-broth. Transformants were selected on L-plates supplemented with 1.5% agar and containing 100 μg/ml ampicillin. The concentration of tetracycline added to L-plates was 10 μg/ml. Complete medium YPG for growth of yeast contained 1% yeast extract, 2% peptone, and 2% glucose. Yeast minimal medium, YMB, contained 0.67% yeast nitrogen base (Difco, Detroit, USA) and 2% sugar (lactose, cellobiose, starch or glucose). The final concentration of amino acids added was as described (24). The solidifying agent on yeast plates was 2% agar (Difco Bacto Agar). In yeast protoplast plating medium 1.2M sorbitol was added as an osmotic stabilizer. The top agar used in plating the yeast protoplasts for regeneration was prepared as minimal medium but using 3% purified agar (Difco) as a solidifying agent.

All methods unless otherwise specified are as described in Maniatis et al. 1982 (25).

Isolation and characterization of the cellulolytic genes from the fungus *T. reesei*

Polyadenylated (polyA+) messenger RNA isolated from *T. reesei* mycelia actively producing cellulases directs in the in vitro synthesis—in a rabbit reticulocyte lysate—of a number of large polypeptides that are precipitated by antibody prepared against purified cellulolytic enzymes. Messenger RNA isolated from repressed glucose grown mycelia does not direct the synthesis of these cellulase-specific polypeptides. This difference between induced and repressed populations was used to identify a collection of hybrid λ phages containing *T. reesei* genes strongly expressed during production of cellulolytic enzymes.

For the isolation of cellulase-specific, induced mRNAs *T. reesei* (strain VTT-D-80133) was grown as described by Bailey and Nevalainen (26) except that the medium contained 2% lactose 2% of a soluble extract of distillers spent grain. Samples taken during cultivation were assayed for activity against dyed Avicel, hydroxyethylcellulose (HEC) and for soluble protein (26). Estimation of reducing sugars was by the method of Sumner (27).

Cellular RNA from mycelia was isolated by a modification of the method of Ohi and Short (28). The frozen mycelia was ground to a fine powder under liquid nitrogen and suspended in a buffer containing 20 mM Tris-HCl (pH 7.6), 0.1M NH 1 mM Mg (OAc) , 10 mM Na-iodoacetate, 0.5 mg/ml polyvinylsulfate and 2% Na-dodecyl sulfate (SDS). Following incubation at 37° C. for 30 minutes, insoluble material was removed by centrifugation at 13000 g for 10 minutes.

The poly(A)+fraction was purified by chromatography through an oligo(dT) cellulose column (Bethesda Research Laboratories (29) and in vitro translation was carried out with a rabbit reticulocyte lysate using $^{35}$S-methionine (Amersham International Ltd) (30). Immunoprecipitation was carried out according to Dobberstein (31) using antiserum prepared against purified CBH I, CBH II or ENDO II, or with the corresponding preimmune serum.

Table 1 shows the molecular weights of proteins precipitated by antiserum against specific cellulases analysed on 7.5–15% SDS polyacrylamide gels (32).

TABLE 1

| Antiserum | In vivo | In vitro |
|---|---|---|
| CBH I | 71 000 | 67 000 |
| CBH II | 63 000 | 48 000 |
| ENDO II | 62 000 | 53 000 |

The construction of the *T. reesei* gene bank was carried out as follows.

Conidia of *Trichoderma reesei* were germinated in a liquid medium containing 1.5% KH PO , 0.5% (NH ) SO , 0.06% MgSO$_4$.7H$_2$O, 0.06% CaCl$_2$, 0.15% proteose peptone, 0.03% urea, 2% sucrose and minimal salts. Cultures were incubated with shaking at 29° C. for about 12 h. The isolation of nuclei was carried out using a slightly modified method of Hautala et al. (33). DNA was isolated from a crude nuclear pellet obtained by differential centrifugation of homogenized mycellium. The crude nuclear pellet was treated with SDS-amylase solution (100 mM EDTA pH 8.0, 140 mM NaCl, 1% Nadecylsulfate and 3.3% α-amylase obtained from Merck, Darmstadt, FRG) for 1 h at 37° C. Proteinase K (final concentration 0.8% w/v) was then added and incubation was continued for 2 h at 37° C. with gentle shaking. After incubation, cell debris was removed by centrifugation and DNA was precipitated from the supernatant with ethanol. The DNA was then purified by CsCl centrifugation. The chromosomal DNA from *T. reesei* was partially digested with MoI and sized by sucrose density gradient centrifugation. Fifteen-20 kb fragments were ligated to Bam HI-cleaved λ 1050 DNA. In vitro packaging of the recombinant molecules was carried out using packaging extracts prepared by the method of Hohn as described by Maniatis et al. (25).

Recombinant phages were transferred from the agar to nitrocellulose filters (Schleicher & Schüll, BA 85) as described by Benton and Davis (34). cDNAs made from induced mRNA (described earlier) and from mRNA isolated from fungus grown in the presence of glucose were used as probes. cDNA first strand synthesis was carried out by the procedure of Efstradiatis et al. (35) but using 10 μCi of 32 pαATP per 50 μl reaction. The in situ plaque hybridization was carried out according to Maniatis et al. (25). Hybridization was detected by autoradiography of the filters on Kodak X-OMAT film. Positive plaques were picked into 1 ml of SM (25) and a drop of chloroform and stored at −4° C.

Hybrid phage hybridizing only to cDNA made with induced mRNA containing cellulase coding sequences were purified extensively and retested by hybridization to both probes. A number of different hybrid clones that hybridized strongly to the induced cellulase probe were identified and selected for further analysis.

The hybrid phages containing genes induced when the fungus produces cellulases were first grouped according to their restriction enzyme patterns. Then the particular cellulase gene in each group was identified by hybrid selection of messenger RNA.

DBM paper was obtained from Schleicher and Schüll (Keene, NH) and activated according to the maker's instructions. Binding of DNA to the activated paper and RNA hybridization and elution was carried out according to Maniatis et al. (25). RNA was translated with a rabbit reticulocyte lysate supplied by Amersham International Ltd. and the proteins produced were labeled with $^{35}$S-methionine. The proteins were analysed by autoradiography on Kodak X-OMAT film after separation on a 7–15% polyacrylamide gradient denaturing gel.

The size of the proteins obtained from particular phage by hybrid selection and their cross reaction with specific antiserum is shown in Table 2.

TABLE 2

| Hybrid Phage No. | 44A | W17A | W12A |
|---|---|---|---|
| Mol. weight of major protein produced from hybrid selected message | 67 000 | 48 000 | 53 000 |
| Cross reaction of major protein with antisera against | | | |
| CBH I | + | − | − |
| CBH II | − | + | − |
| ENDO II | − | − | + |

Single and double digests of the clone 44A, were analyzed on 0.6% and 1.5% agarose gels. The fragments were electrophoretically transferred to Gene Screen membranes (New England Nuclear, MA) and hybridized to the induced cDNA probe as instructed by the manufacturer.

Figure 2:
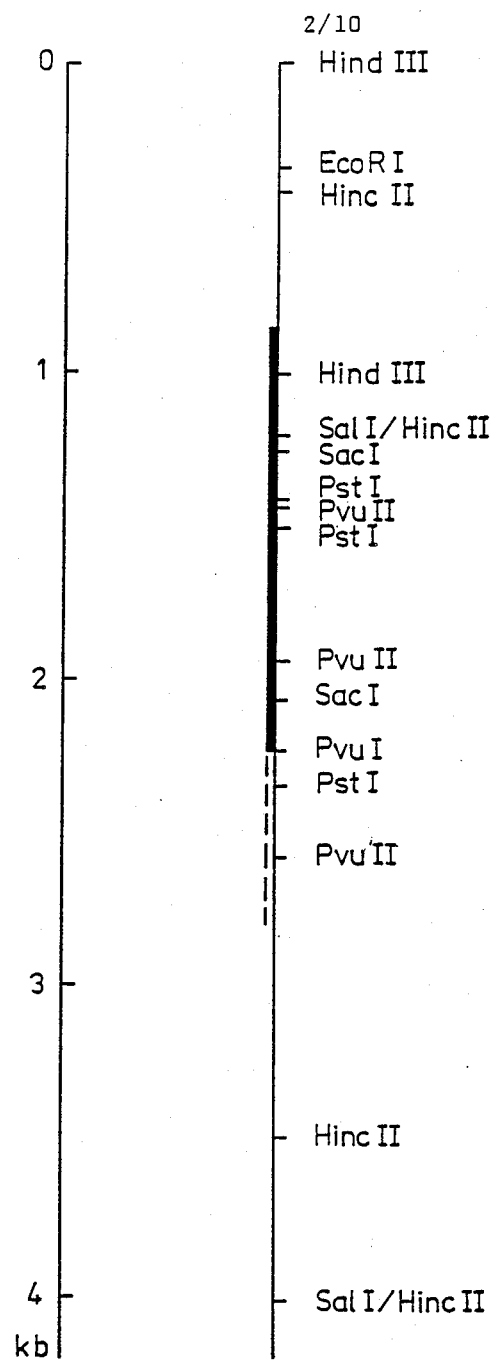
FIG. 2 shows the restriction map of *T. reesei* cellobiohydrolase II (CBH II) chromosomal gene. The coding region is marked with thickened line.
Figure 3:
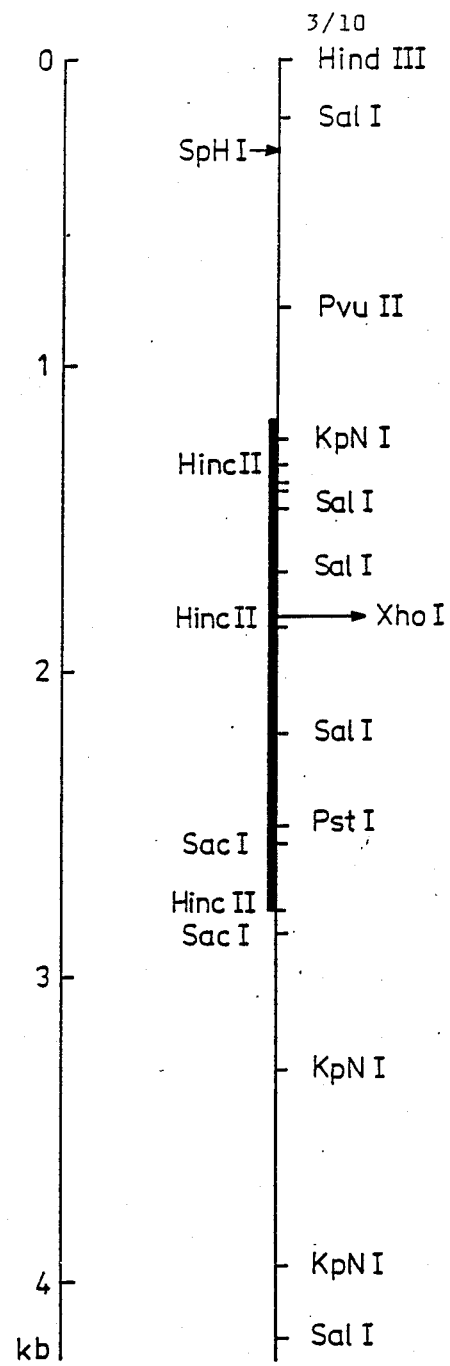
FIG. 3 shows the restriction map of *T. reesei* endoglucanase II (ENDO II) chromosomal gene. The coding region is marked with thickened line.

This procedure permitted the construction of restriction enzyme maps of the three cellulose genes. These restrictions enzyme maps are shown in FIGS. 1, 2 and 3.

The nucleotide sequence of the CBH I, CBH II and ENDO II genes was generated by dideoxy sequencing (36) using restriction enzyme fragments or DNA fragments obtained by the "shotgun" procedure (37).

The construction of a yeast vector containing the CBH I chromosomal gene

The hybrid phage 44A (11) DNA containing the CBH I of *Trichoderma reesei* hypercellulolytic mutant strain VTT-D-80133, was digested with Pst I to give a mixture of fragments one of which being about 12 kb and containing the entire CBH I gene with its own regulatory sequences. The resulting DNA-fragments were ligated with the yeast cosmid p3030 digested partially with the same enzyme.

The yeast strain OL1 was transformed to his+with the DNA-mixture described above. Transformation was carried out essentially as described by Gerbaud et al. (38). Transformed cells were plated on yeast animal medium with leucin and uracil but lacking histidine.

The clones were further tested in situ plaque hybridization for the presence of the CBH I gene originated from *T. reesei*.

Figure 4:
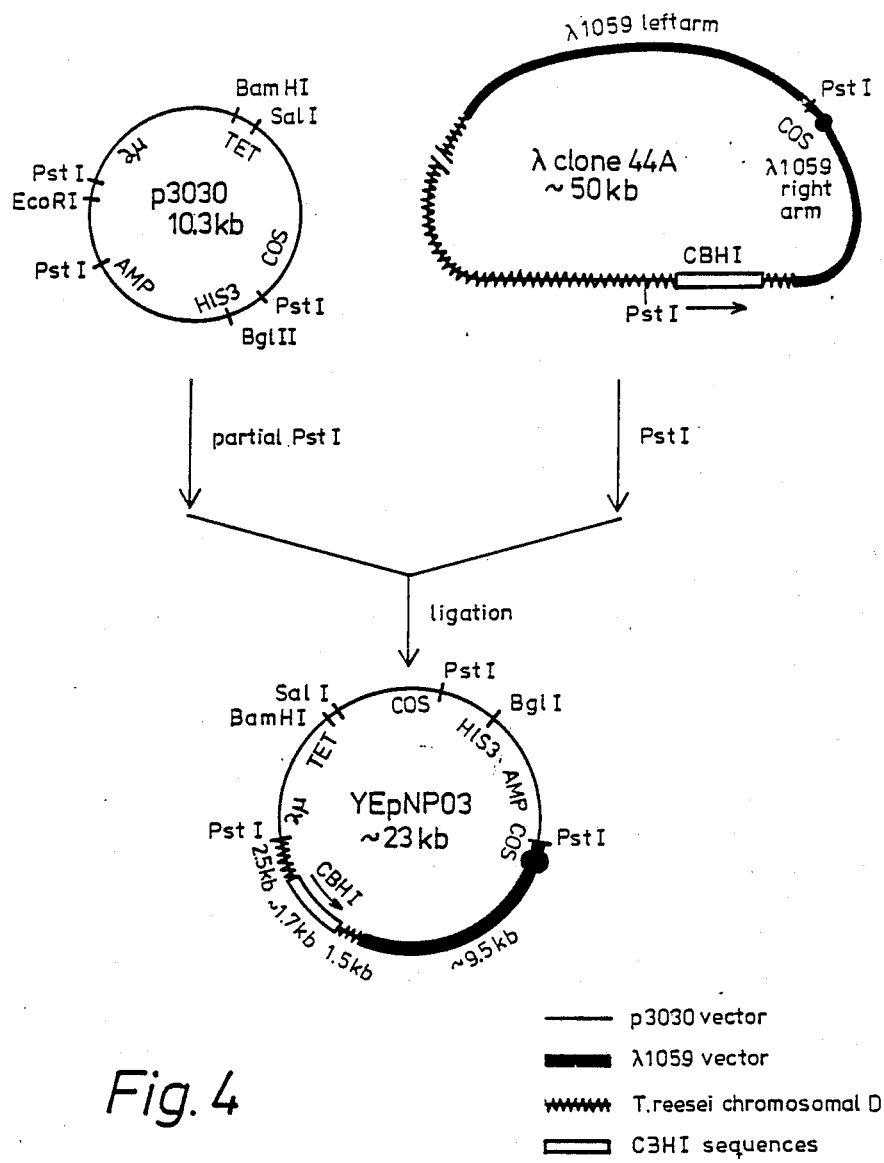
FIG. 4 shows the construction of plasmid YEpNPO3 for expression of a chromosomal copy of CBH I gene from *T. reesei* in yeast.

The presence of an intact CBH I gene in yeast was ensured by isolating total DNA (39) from a transformant colony and digesting it with restriction enzymes Bgl II and Hinc II. DNA was transferred to nitrocellulose filter (40) from agarose gel and hybridized to a M13 probe (41) containing the 0.7 kb Eco RI fragment from CBH I gene. FIG. 4 shows the construction of a hybrid plasmid containing the CBH I gene.

Isolation of full length cDNAs coding for the enzymes CBH I, CBH II and ENDO II

A cDNA bank from *T. reesei* was made from induced mRNA isolated from cells as described earlier. However, after the frozen mycelia had been ground under liquid nitrogen it was suspended in 5 volumes a guanidinium isothiocyanate buffer as described by Maniatis et al. (25). The RNA preparation was then carried out as described (42). cDNA first strand synthesis was carried out according to Maniatis (25) and the second strand was carried out according to Gubler and Hoffmann (43). The double stranded cDNA was then treated with T$_4$-polymerase to give blunt ends and small cDNAs less than 500 nucleotides long removed by passage through a CL-4B column (Pharmacia). Long cDNAs were then ligated to a Sma I digested and phosphatase treated preparation of pUC 8 vector. The ligation mixture was used to transform *E. coli* strain JM 105 and the cDNA bank was stored on nitrocellulose filters.

Full length cDNAs coding for CBH I, CBH II and ENDO II were isolated from a cDNA bank using specific restriction fragments as probes. For the identification of CBH I, a radioactive Eco RI-Hind III fragment from the 5 end of the chromosomal gene was used to identify long cDNAs. A plasmid pTTO1 from a clone containing sequences homologous to this Eco RI-Hind III fragment was further characterized by sequencing of the cDNA ends by double stranded dideoxy sequencing. 1 μg of purified plasmid was denatured in 0.4M NaOH at room temperature for 5 minutes at a concentration of 100 ng/μl. 5 μl of sequencing or reverse sequencing primer (Amersham) was added and the mixture was precipitated with ethanol. After washing the pellet was resuspended in 10 μl at 14 mM Tris pH 8-7 mM MgCl$_2$. Sequencing reactions were done according to general methods (36) except that temperature was kept at 37° C. CBH II cDNAs were isolated using a Pvu II fragment from the 5' end of the chromosomal gene and the plasmid pTT09 characterized an for the CBH I cDNA. ENDO II cDNAs were identified using a Kpn I-Sal I fragment from the 5' end of the gene and plasmid pTT11 also characterized as for the CBH I cDNA. All cDNAs were then sequenced to determine that their sequence corresponded to that of the gene from which they are transcribed. The DNA sequences of CBH II and ENDO II cDNAs are shown in FIGS. 5 and 6. The cDNA sequence of CBH I was identical to that already described (10).

Figure 7:
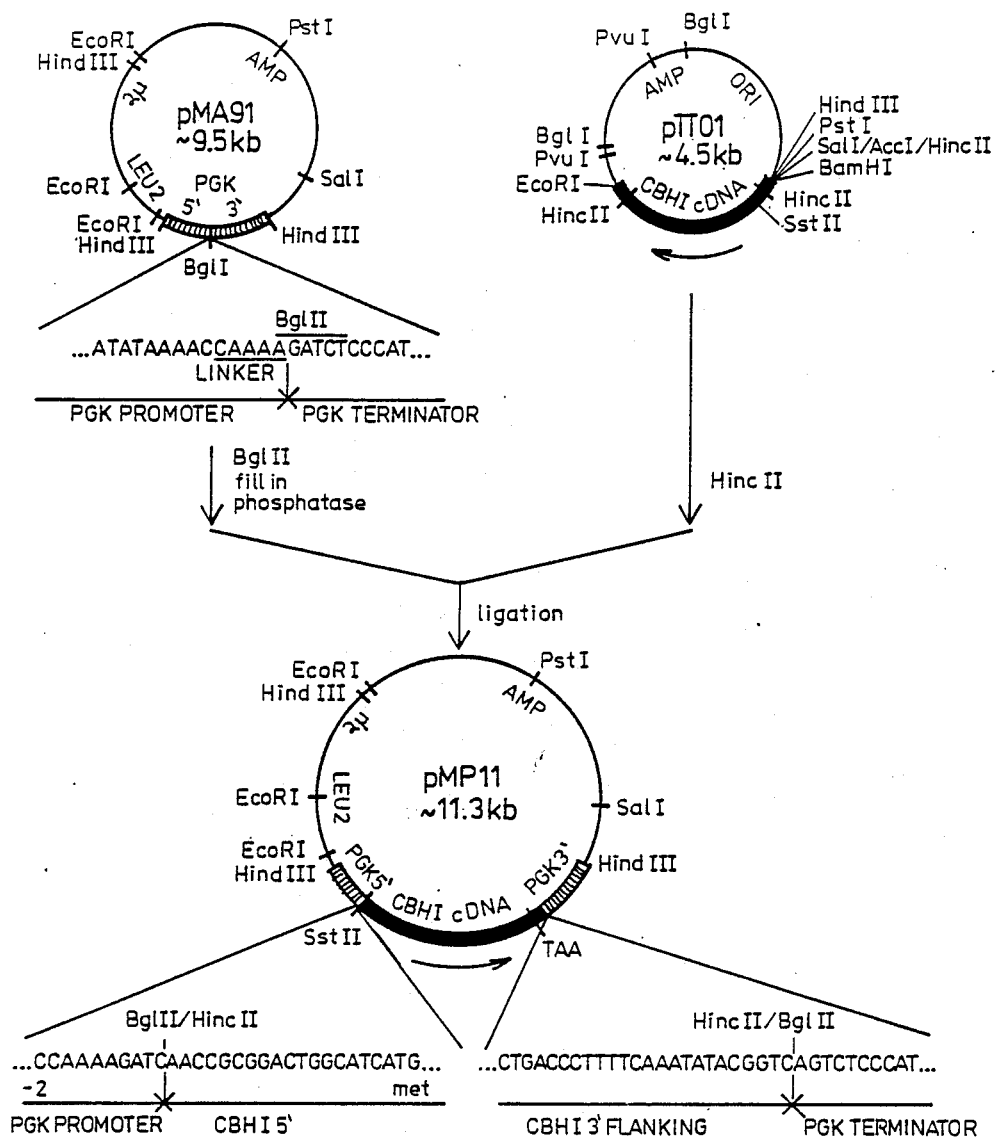
FIG. 7 shows the construction of plasmid pMP11 for expression of *T. reesei* CBH I in yeast.

The construction of expression vectors containing cDNAs for the production of fungal cellulases in yeast The efficient yeast expression vector pMA 91 has been assembled using the regulatory sequences of the yeast phosphoglycerokinase (PGK) gene (23). The sequences coding for the amino acid sequence of the enzyme have been removed from the gene and replaced by a single Bgl II site. This deleted gene has then been inserted into a yeast/coli shuttle plasmid.

a) CBH I expression vector (FIG. 7)

Figure 8:
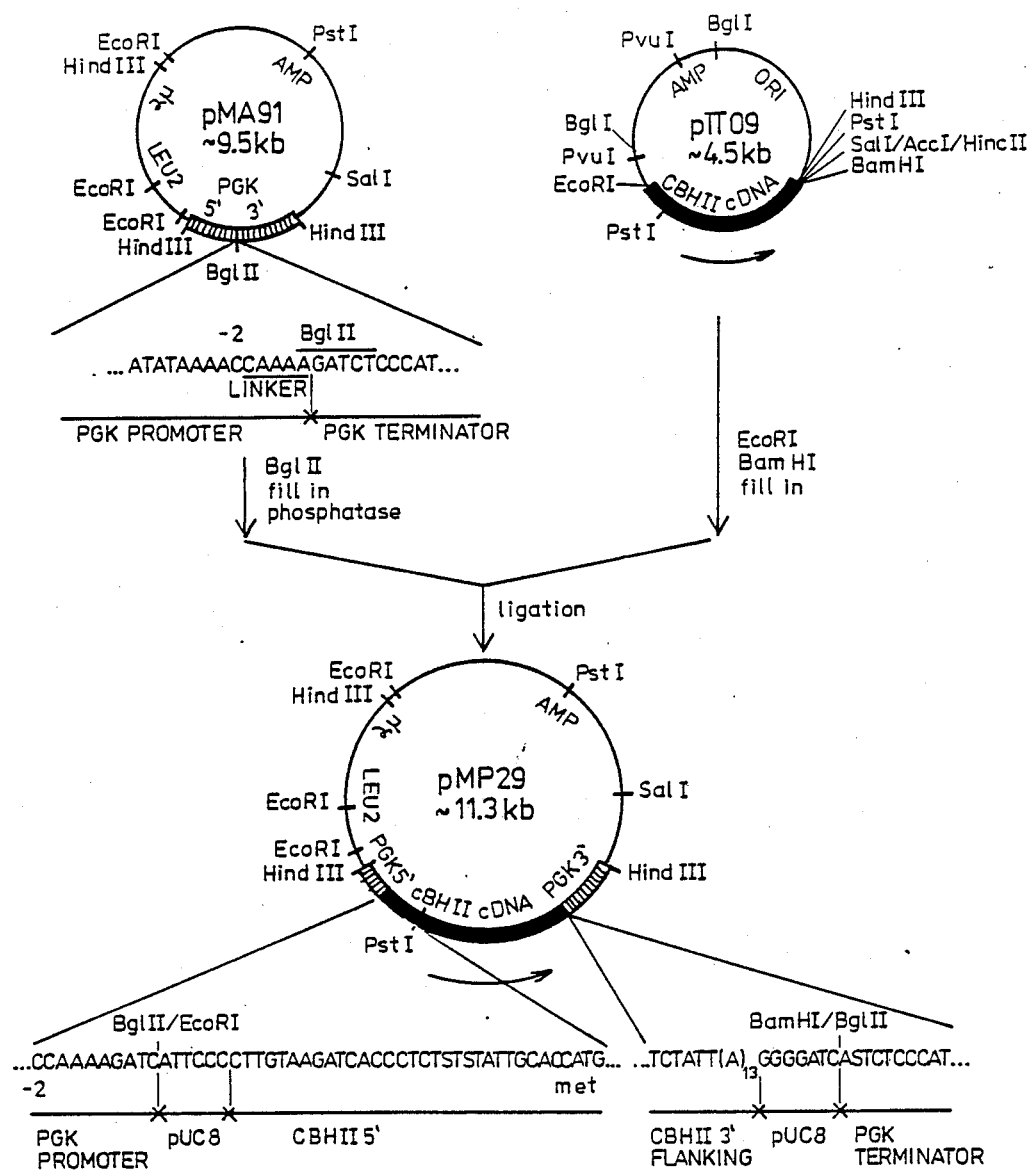
FIG. 8 shows the construction of plasmid pMP29 for expression of *T. reesei* CBH II in yeast.

The CBH I cDNA was removed from plasmid (pTTO1 FIG. 7) by digestion with Hinc II and the cDNA fragment isolated from an agarose gel.

pMA 91, the expression vector was cleaved with Bgl II and the ends were filled in with the Klenow fragment. The vector was treated with phosphatase, ligated to the cDNA and transformed into *E. coli* strain HB1O1 by selection for expression of the vector leucine gene (FIG. 7). Plasmid DNA was isolated from a number of transformants and those clones containing the cDNA insert in the correct orientation with respect to the PGK promotor - as identified by restriction enzyme analysis - were retained. DNA from one of these clones (pMP 11) was then transformed into yeast strain MT 302-lc by the method described earlier by selection of the leucine marker of pMA 91 resulting in strain VTT-RC-84011.

b) CBH II expression vector (FIG. 8)

CBH II cDNA was removed from plasmid pTT 09 using Eco RI and Bam HI. The ends of the DNA were filled in with Klenow fragment. The cDNA fragment was then isolated from an agarose gel and ligated to the vector pMA 91 prepared as for CBH I.

The ligation mix was transferred into HB1O1 and clones containing the cDNA in the correct orientation identified. FIG. 8 shows the DNA sequence at the junctions between pMA 91 and the cDNA.

Plasmid pMP 29 with the cDNA in the correct orientation was then used to transform yeast MT302-lc by selection for the leucine marker to give strain VTT-RC-84012.

Figure 9:
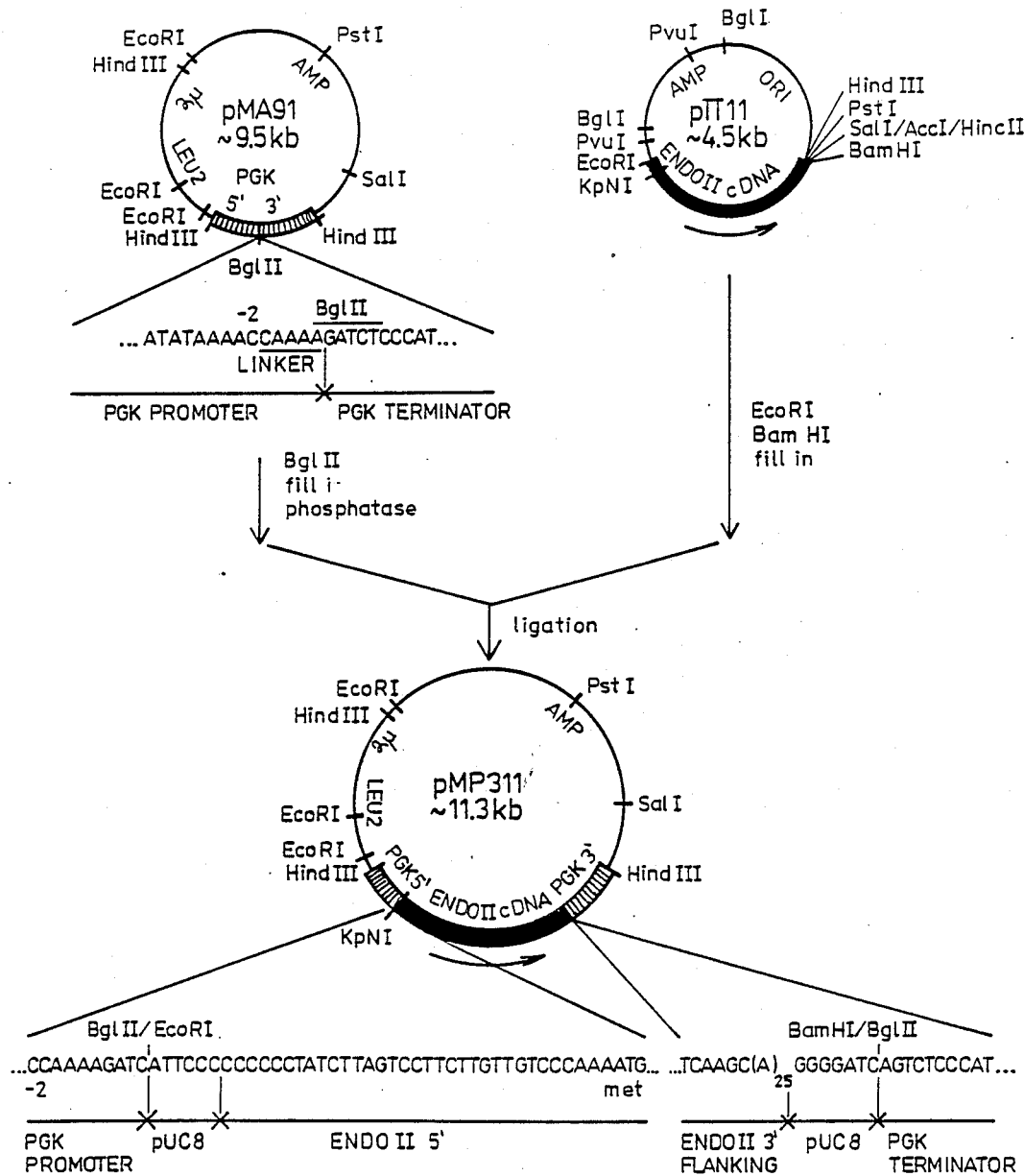
FIG. 9 shows the construction of plasmid pMP311 for expression of *T. reesei* ENDO II in yeast.

(c) ENDO II expression vector (FIG. 9)

The ENDO II cDNA was transferred to p 91 exactly in the same way as CBH II cDNA. FIG. 9 shows the DNA sequences at the junctions between pMA 91 and the ENDO II cDNA. The plasmid, pMP 311 containing the ENDO II cDNA in the correct orientation was transferred to yeast as described earlier to give strain VTT-RC-84013.

Culturing the hybrid yeast strains to produce the cellulolytic enzymes, CBH I, CBH II and ENDO II Strain VTT-RC-84001 containing YEpNP03 was grown in a yeast minimal medium with leucine and uracil for three days after which complete medium (⅓ volume) was then added to allow the cells to pass through one more division.

Strains VTT-RC-84011 (CBH I cDNA), VTT-RC-84012 (CBH II cDNA) and VTT-RC-84013 (ENDO II cDNA) were grown in a yeast minimal medium containing arginine, histidine and adenine for three days after which complete medium ⅓ volume was added to allow the cells to pass through one more division. The final volume of the cultures was about 150 ml.

Preparation of different fractions for analysis of the location of enzyme activity Three fractions were prepared from hybrid yeast cultures for analysis of enzyme activity. Fraction 1 comprised the growth medium without the cells. Fraction 2 comprises the supernatant left when protoplasts are pelleted and fraction 3 comprises the supernatant of lysed protoplasts.

After cultivation yeast cells were collected by centrifugation and the supernatant was saved (Fraction 1). The resulting pellet was washed twice with distilled water and 1.2M sorbitol. The pellet was then resuspended in protoplasting buffer (1.2M sorbitol, 10 mM Tris and 10 mM CaCl, pH 7.6) and Zymolyase 60000 was added at a concentration of 30 μg/ml of protoplasting suspension. Suspension was incubated in a waterbath at 37° C. for 60 minutes with gentle shaking. The protoplasts so formed were pelleted and the resulting supernatant (periplasmic cell contents) (Fraction 2) saved for enzyme activity determinations. In some cases fractions 1 and 2 were concentrated by ultrafiltration (Amicon). Protoplast pellets were washed with cold 1.2M sorbitol and resuspended in 1.2 ml of 5 mM citrate buffer pH 5.0, pelleted and the supernatant was saved (Fraction 3).

Measurement of cellulase enzyme activity produced by the hybrid yeasts

1 CBH I activity from VTT-RC-84001

The three different fractions were tested for CBH I enzyme activity using amorphous ball milled cellulose which is attached only by cellobiohydrolases (44). The total protein concentration of the samples was about 300 μg/ml. Hydrolysis of the substrate caused by active cellobiohydrolase enzyme was measured by following the change in absorbance at 620 nm. CBH I type activity was found only in fraction 2, the periplasmic or intramural space.

Figure 10:
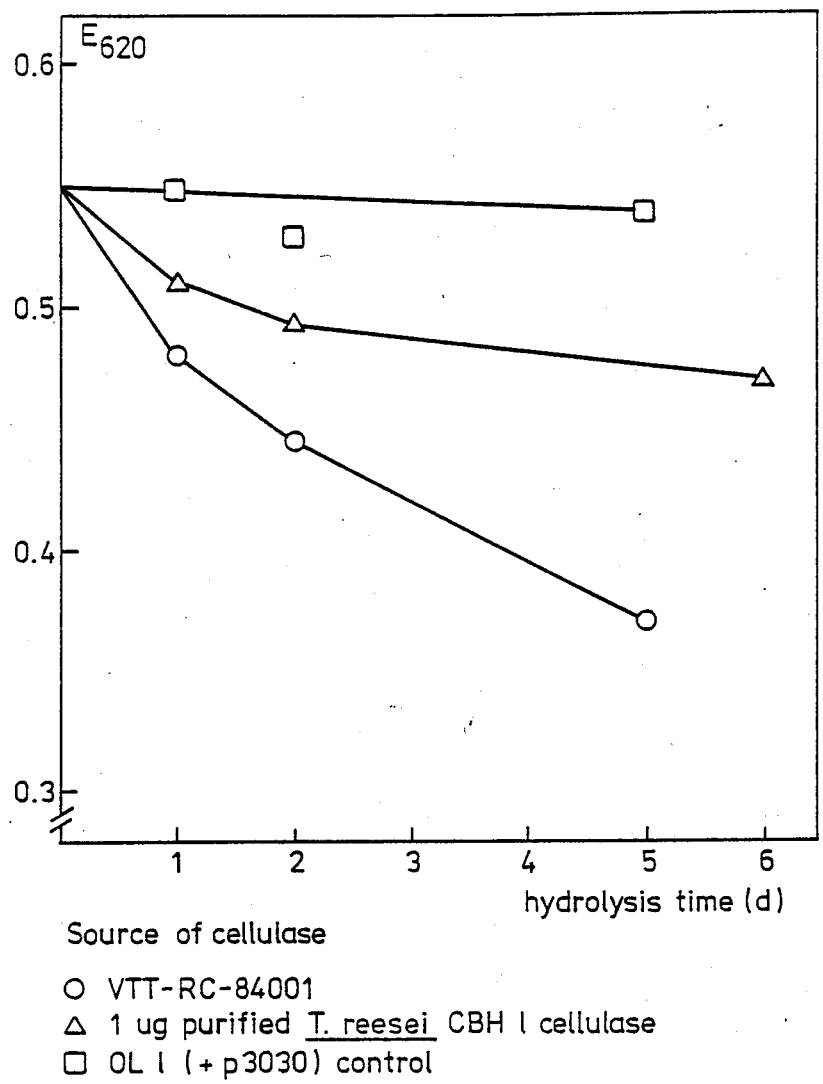
FIG. 10 shows the enzyme activity of CBH I produced by the yeast strain VTT-RC-84001.

FIG. 10 shows the activity of the CBH I enzyme produced by the yeast strain VTT-RC-84OO1 and secreted into the intramural space as compared to the control yeast containing only vector p3030 DNA and 1 μg of *Trichoderma* BH I. This Figure shows that the hybrid yeast strain produces active CB I which appears to be at least as resistant to incubation at 50° C. for 3 days as in the native enzyme. The CBH I produced by the yeast represents 1–2% of the protein of intramural space protein.

As the intron sequences of fungus are different from those of yeast it is not likely that yeast would process off the fungus gene introns. Probably for that reason the product of the chromosomal gene remains in the yeast periasmic space and is not secreted from the cell as is the product coded by the cDNA sequence. This result suggests that transferring the chromosomal gene coding for CBH I to yeast, results in the production of a smaller protein, which, however, has the safe type of activity as the full length cellulase.

2 CBH I activity from VTT-RC-84011

The three different fractions were tested for CBH I enzyme activity as just described. However, in this case, most of the CBH I type activity was found in the growth medium. The results, with a final protein concentration during hydrolysis of 5 μg/ml is very similar to that shown in FIG. 10. The CBH I enzyme produced with this construction represented 1-5% of total cell protein.

3 CBH II activity from VTT-RC-84012

The three different fractions were tested from cellobiohydrolase activity as described for strain VTT-RC-8401. As with strain VTT-RC-84011, most of the cellobiohydrolase type activity was found in the growth medium. The results with a final protein concentration of 10 μg/ml is similar to than shown in FIG. 10. The CBH II enzyme produced with this construction represented 1-5% of total cell protein.

4 ENDO II activity from VTT-RC-84013

The three different fractions were tested for endoglucanase activity by following the hydrolysis of 0.1% 8-glucan at 50° C.

The reducing sugars liberated in 5 minutes (overnight) were measured as glucose using the dinitro saliylic acid method (45). Most of the ENDO II activity was found secreted into the growth medium. The ENDO II enzyme produced with this construction represented 1-5% of total cell protein.

It is considered that the invention and many of its attendant advantages will be understood from the foregoing description and that it will be apparent that various changes may be made in the steps of the described method for mixture protein synthesis without departing from the spirit and scope of the invention or sacrificing all of its material advantages, the method herein before described being merely a preferred embodiment.

REFERENCES

1. B.S. Montenecourt, 1983, Technol. in Biotechnology 1, 156-161.
2. ENARI, T-M. Microbiol. Cellulases p. 183-223. In: Microbiol. Enzymes and Biotechnologes. William M. Fogarty (ed.). Applied Science Publishers, London and New York.
3. Shoemaker, S. P. and Brown, R. D. Jr (1978a) Biochim. Biophys. Acta 523, 133-146.
4. Shoemaker, S. P. and Brown, R. D. Jr. (1978b) Biochim. Biophys. Acta 523, 147-161.
5. Fägerstam, L. and Petterson, L. G. (1979) FEBS Lett. 98, 363-367.
6. Fägerstam, L. and Petterson, L. G. (1980) FEBS Lett. 119, 97-100.
7. Sprey, B. and Lambert, C. (1983) FMS Microbiol. Lett. 18, 217-222.
8. Chanzy, H., Henrissat, B., Vuong, R. and Schulein, M. (1983) FEBS Lett. 153, 113-118.
9. Nummi, M., Niku-Paavola, M. L., Lappalainen, A., Enari, T. M. and Raunio, V. (1983) Biochem. J. 215, 677-683.
10. Shoemaker, S., Schweickart, V., Ladner, M., Gelfand, D., Kwok, S., Myambo, K. and Innis, M. (1983) Biotechnol. 1. 691-696.
11. Teeri, T., Salovuori, I. and Knowles J. (1983), Biotechnol. 1, 696-699.
12. Penttilä M. E., Nevalainen, K. M. H, Raynal, A. and Knowles, J. C. K. 1984: Molec., Gen Genetics, in press.
13. Hitzeman, R. A., F. E. Hagie, H. L. Levine, D. V. Goeddel, G. Ammerer & B. D. Hall: Expression of a human gene for interferon in yeast. Nature 293, 717-722 (1981).
14. Valenzuela, P., A. Medina, W. J. Rutter, G. Ammerer & B. D. Hall: Synthesis and assembly of hepatitis B virus surface antigen particles in yeast. Nature 298, 347-350 (1982).
15. Mellor, J., M. J. Dobson, M. A. Roberts, M. F. Tuite, J. S. Emtage, S. White, P. A. Lowe, T. Patel, A. J. Kingsman & S. M. Kingsman: Efficient synthesis of enzymatically active calf chymosin in Saccharomyces cerevisiae. Gene 24 (1983): 1-14.
16. K. K. Thomsen, 1983, Carlsberg Res. Commun. 48 p. 545-555.
17. Mandels, M., Weber, J. and Parrek, R. (1971) Appl. Microbiol. 21, 152-154.
18. Nevalainen K. M. H. 1981: Appl. Envron. Microbiol. 41: 595-596.
19. Karn, J., Brenner, S., Barnett, L. and Cesaveni, G. 1980. Novel bacteriophage λ cloning vector. Proc. Natl. Acad. Sci. 77:5172-5176.
20. Messing, J., Crea, R., and Seeburg, P. H. 1981. A system for shotgun DNA sequencing. Nucleic Acids Res. 9: 309-321.
21. Vieira, J. and Messing, J. 1982: Gene 19:259-268.
22. Boy-Marcotte, E., Jaquet, M, (1982) A dictyostelium discoidem DNA fragment complements a Saccharomyces cerevisiae ura 3 mutant. Gene 20:433-440.
23. Mellor, J., Dobson, M. J., Roberts N. A., Tuite, M. F., Emtage, J. S., White, S., Lowe, P. A., Patel, T., Kingsman, A. J. and Kingsman, S. M. 1983. Efficient synthesis of enzymatically active calf chymosin in Saccharomyces cerevisiae. Gene 24: 1-14.
24. Sherman, F., Fink, G. R. and Hicks J. B. 1981. Methods in yeast genetics. Cold Spring Habor Laboratory, New York. p. 62.
25. Maniatis, T., Fritsch, E. F. and Sambrook, J. 1982. Molecular cloning: A laboratory manual. Cold Spring Harbor Laboratory, Cold Spring Harbor, N.Y.
26. Bailey, M. J. and Nevalainen, K. M. H. 1981. Induction, isolation and testing of stable Trichoderma reesei mutants with improved production of solubilizing cellulase. Enzyme Microb. Technol 3:153-157.
27. Sumner, J. B. and Somers, G. F. (1949) in Laboratory experiments in biological chemistry 2nd ed. pp. 38-39, Academic Press, New York.
28. Ohi, S., and Short, J. 1980. A general procedure for preparing messenger RNA from eukaryotic cells without using phenol. J. Appl. Microbiol. 2:398-413.
29. Aviv, H. and Leder, P. (1972) Proc. Natl. Acad. Sci. 69 1408-1412.
30. Pelham, H. R. B. and Jackson, R. J. (1976) Env. J. Bochem. 67 pp. 247-256.

31. Dobberstein, B., Garoff, H. and Wawen, G. (1979) Cell 17, 759–769.
32. Laemmli, U. 1970. Cleavage of structural proteins during the assembly of bacteriophage T4. Nature 227: 680–685.
33. Hautala, J. A., Corner, B. H., Jacobson, J. W., Patel, G. L. and Giles, N. H. 1977. Isolation and characterization of nuclei from Neurospova crassa. J. Bacteriol. 130: 704–713.
34. Benton, W. D. and Davis, R. W. 1977 Screening $\lambda_{gt}$ recombinant clones by hybridization to single plaques in situ. Science 196:180–182.
35. Efstradiatis, A., Kafatos, F. C., Maxam, A. M. and Maniatis, T. 1976. Enzymatic in vitro synthesis of globin genes. Cell 7:279–288.
36. Sanger, F., Nicklen, S. and Coulson, A. R. 1977. Proc. Natl. Acad. Sci. U.S.A. 74:5463–5467.
37. Deiniger, P. L. 1983: Anal. Biochem. 129: 216–223.
38. Gerbaud, C., Faurnier, P., Blanc, H., Aigle, M., Heslot, H. and Guerinau, M. 1979. Gene 5:233–253.
39. Sherman F. Fink, G. R. and Hicks, J. B. 1981: Methods in yeast genetics. Cold Spring Harbor Laboratory, New York, pp. 77–80.
40. Southern, E. M. 1975. J. Mol. Biol 98: 503–517.
41. Hu, N. and Messing, S. 1982. Gene 17:271–277.
42. Chirgwin, J. M., Przybyla, A. E., MacDonald, R. J. and Rutter, W. J. 1979. Isolation of biologically active ribonucleic acid from sources enriched in ribonuclease. Biochemistry 18: 5294–5299.
43. Gubler and Hoffman 1983: Gene 25:263
44. Nummi, M., Fox, P. C., Niku-Paavola, M. L., and Enari, T-M. 1981 Anal. Biochem. 116:133–136.
45. Kirsop, B. H. 1953: J. Inst. Brewing 59:378.

What is claimed is:

1. A substantially pure DNA sequence or its single or multiple base substitutions, deletions, insertions or inversions, encoding an amino acid sequence comprising the mature cellobiohydrolase II protein amino acid sequence shown in FIG. 5, or a portion thereof having cellobiohydrolase II activity.

2. The DNA sequence of claim 1, additionally comprising a DNA sequence encoding an amino acid sequence comprising the cellobiohydrolase II signal sequence shown in FIG. 5, or a portion thereof having cellobiohydrolase II signal sequence activity.

3. A substantially pure DNA sequence comprising the cDNA sequence shown in FIG. 5 encoding an amino acid sequence comprising the mature cellobiohydrolase II protein amino acid sequence, or a portion thereof which encodes an amino acid sequence having cellobiohydrolase II activity.

4. The DNA sequence of claim 3, additionally comprising the cDNA sequence shown in FIG. 5 which encodes an amino acid sequence comprising the cellobiohydrolase II signal sequence, or a portion thereof which encodes an amino acid sequence having cellobiohydrolase II signal sequence activity.

5. The DNA sequence of claim 3, wherein said cDNA is a cDNA copy of Trichoderma reesei mRNA encoding cellobiohydrolase II.

6. The DNA sequence of claim 4, wherein said cDNA sequence shown in FIG. 5 which encodes an amino acid sequence comprising the cellobiohydrolase II signal sequence, is a cDNA copy of Trichoderma reesei mRNA encoding the cellobiohydrolase II signal sequence.

7. A substantially pure DNA sequence encoding an amino acid sequence comprising the cellobiohydrolase II signal sequence shown in FIG. 5, or a portion thereof having cellobiohydrolase II signal sequence activity.

8. A recombinant DNA vector comprising the DNA sequence of any of claims 1, 2, 3, 4, 5, 6, or 7.

9. A yeast host transformed with the vector of claim 8.

10. The yeast host of claim 9, wherein said host is of the genus Saccharomyces.

11. The yeast host of claim 10, wherein said Saccharomyces host is S. cerevisiae.

12. A method for constructing a recombinant DNA vector, comprising ligating into a suitable plasmid or phage the DNA sequence of any of claims 1, 2, 3, 4, 5, 6, or 7.

13. A method for DNA expression, comprising transforming a yeast host with a recombinant DNA vector comprising the DNA sequence of any of claims 1, 2, 3, 4, 5, 6, or 7, and culturing said host under conditions wherein said DNA sequence is transcribed and translated.

* * * * *